United States Patent
Johannaber et al.

(10) Patent No.: US 11,020,246 B2
(45) Date of Patent: Jun. 1, 2021

(54) FORCE AND ROTATION SENSING DEVICE AND METHOD

(71) Applicant: Zimmer, Inc., Warsaw, IN (US)

(72) Inventors: Kenneth D. Johannaber, Reno, NV (US); Rida Hariri, Reno, NV (US); Derek Dalbey, Reno, NV (US); John Minck, Jr., Reno, NV (US)

(73) Assignee: Zimmer, Inc., Warsaw, IN (US)

( * ) Notice: Subject to any disclaimer, the term of this patent is extended or adjusted under 35 U.S.C. 154(b) by 207 days.

(21) Appl. No.: 15/879,164

(22) Filed: Jan. 24, 2018

(65) Prior Publication Data

US 2018/0214283 A1 Aug. 2, 2018

Related U.S. Application Data

(60) Provisional application No. 62/453,772, filed on Feb. 2, 2017.

(51) Int. Cl.
| | | |
|---|---|---|
| *A61F 2/46* | (2006.01) | |
| *A61F 2/38* | (2006.01) | |
| *A61B 90/00* | (2016.01) | |

(52) U.S. Cl.
CPC ............ *A61F 2/4657* (2013.01); *A61B 90/37* (2016.02); *A61F 2/3859* (2013.01);
(Continued)

(58) Field of Classification Search
CPC .. A61F 2/46; A61F 2/4657; A61F 2/38; A61F 2/3859
See application file for complete search history.

(56) References Cited

U.S. PATENT DOCUMENTS

| | | | |
|---|---|---|---|
| 2010/0063508 A1* | 3/2010 | Borja ................... | A61B 17/154 606/88 |
| 2010/0217156 A1* | 8/2010 | Fisher ................... | A61B 17/88 600/587 |

(Continued)

FOREIGN PATENT DOCUMENTS

| | | |
|---|---|---|
| CN | 101849864 A | 10/2010 |
| CN | 203182910 U | 9/2013 |

(Continued)

OTHER PUBLICATIONS

"International Application Serial No. PCT US2018 015044, International Search Report dated May 23, 2018", 7 pgs.
(Continued)

*Primary Examiner* — Christopher J Beccia
(74) *Attorney, Agent, or Firm* — Schwegman Lundberg & Woessner, P.A.

(57) ABSTRACT

A force and rotation sensing device can be suitable for measuring a force within a knee joint. A force sensor can measure a force exerted between opposing surfaces of a housing. A force display positioned on the housing can visually represent a value of the measured force, such as with a dual-sided light-emitting diode display that is visible from opposing sides of the housing. A first rotation sensor can measure a flexion/extension position of the housing. A flexion/extension display can visually represent a value of the measured flexion/extension position. In some examples, a zero button can set a reference orientation of the housing, so that the first rotation sensor can measure the flexion/extension position as a relative rotation with respect to the reference orientation. In some examples, circuitry can wirelessly transmit data corresponding to the value of the measured flexion/extension position.

19 Claims, 8 Drawing Sheets

(52) U.S. Cl.
CPC ... *A61B 2090/064* (2016.02); *A61B 2090/372* (2016.02); *A61B 2560/0223* (2013.01); *A61B 2562/0219* (2013.01); *A61F 2/4684* (2013.01); *A61F 2002/4666* (2013.01); *A61F 2002/4668* (2013.01); *A61F 2250/0002* (2013.01)

(56) References Cited

U.S. PATENT DOCUMENTS

| | | | |
|---|---|---|---|
| 2010/0249658 A1* | 9/2010 | Sherman | A61B 5/103 600/587 |
| 2011/0093081 A1* | 4/2011 | Ghana | A61B 17/1764 623/20.14 |
| 2014/0276861 A1 | 9/2014 | Stein et al. | |
| 2014/0296860 A1 | 10/2014 | Stein et al. | |

FOREIGN PATENT DOCUMENTS

| | | |
|---|---|---|
| CN | 105517511 A | 4/2016 |
| CN | 103997963 B | 11/2016 |
| CN | 110248622 | 9/2019 |
| EP | 2237014 | 10/2010 |
| JP | 2010240403 | 10/2010 |
| JP | 2020510465 A | 4/2020 |
| WO | 2010022272 | 2/2010 |
| WO | 2018144282 | 8/2018 |

OTHER PUBLICATIONS

"International Application Serial No. PCT US2018 015044, Written Opinion dated May 23, 2018", 6 pgs.

"European Application Serial No. 18704675.0, Response to Communication pursuant to Rules 161(2) and 162 EPC filed Apr. 14, 2020", 12 pgs.

"Chinese Application Serial No. 201880009908.5, Office Action dated Oct. 10, 2020", w/English translation, 16 pgs.

"International Application Serial No. PCT US2018 015044, International Preliminary Report on Patentability dated Aug. 15, 2019", 8 pages.

"Australian Application Serial No. 2018214820, First Examination Report dated Sep. 30, 2019", 3 pages.

"Australian Application Serial No. 2018214820, Response filed Nov. 12, 2019 to First Examination Report dated Sep. 30, 2019", 18 pages.

"Japanese Application Serial No. 2019-541782, Notification of Reasons for Refusal dated Dec. 1, 2020", with English translation, 7 pages.

"Canadian Application Serial No. 3,052,264, Office Action dated Jan. 8, 2021", 4 pgs.

* cited by examiner

FORCE AND ROTATION SENSING DEVICE AND METHOD

CROSS-REFERENCE TO RELATED APPLICATION

This application claims the benefit of U.S. Provisional Application No. 62/453,772, filed Feb. 2, 2017, which is hereby incorporated by reference in its entirety.

FIELD OF THE DISCLOSURE

The present disclosure relates to a force and rotation sensing device suitable for measuring a force within a knee joint, and a method of using the same.

BACKGROUND OF THE DISCLOSURE

In a knee surgery procedure, a surgeon can manually position a knee joint at one or more positions between full flexion and full extension, inclusive. In some procedures, the surgeon can visually estimate an angular position for the knee joint.

SUMMARY

In one example of a force and rotation sensing device, an elongate housing can extend along a longitudinal axis. A force sensor can measure a force exerted between opposing surfaces of the housing at a distal portion of the housing. A force display can be positioned on the housing and can visually represent a value of the measured force. A reference surface can be positioned on the housing. The reference surface can define a plane that includes the longitudinal axis. The reference surface can further define a flexion/extension axis as being parallel to the plane and perpendicular to the longitudinal axis. A first rotation sensor can measure a flexion/extension position of the housing. The flexion/extension position can be a rotational position about the flexion/extension axis. A flexion/extension display can be positioned on the housing and can visually represent a value of the measured flexion/extension position.

In one example of a method for measuring force within a knee joint, a reference orientation of a housing can be set against a resected condyle in a knee joint. A distal portion of the housing can be inserted into the knee joint. The distal portion of the housing can include a force sensor. The knee joint can be positioned at a plurality of positions between flexion and extension, inclusive. At each position of the plurality of positions, a measurement of flexion/extension position of the housing can be read from a display on the housing. At each position of the plurality of positions, a measurement of force exerted by the knee joint on a distal portion of the housing can be read from a display on the housing.

In another example of a force and rotation sensing device, an elongate housing can extend along a longitudinal axis. A force sensor can measure a force exerted between opposing surfaces of the housing at a distal portion of the housing. A force display can be positioned on the housing and can visually represent a value of the measured force. The force display can include a dual-sided light-emitting diode display that is visible from opposing sides of the housing. A reference surface can be positioned on the housing and can be formed as one of the opposing surfaces. The reference surface can define a plane that includes the longitudinal axis. The reference surface can further define a flexion/extension axis as being parallel to the plane and perpendicular to the longitudinal axis. A zero button on the housing can set a reference orientation of the housing. A first rotation sensor can measure a flexion/extension position of the housing. The flexion/extension position can be a relative rotational position about the flexion/extension axis with respect to the reference orientation. The first rotation sensor can include at least one of an accelerometer or a gyroscope. A flexion/extension display can be positioned on a proximal end of the housing, opposite the distal portion. The flexion/extension display can visually represent a value of the measured flexion/extension position. A second rotation sensor can measure a varus/valgus position of the housing. The varus/valgus position can be a relative rotational position about the longitudinal axis with respect to the reference orientation. The second rotation sensor can include at least one of an accelerometer or a gyroscope. A varus/valgus display positioned on the proximal end of the housing can visually represent a value of the measured varus/valgus position. Circuitry can wirelessly transmit data corresponding to the value of the measured flexion/extension position and the value of the measured varus/valgus position.

BRIEF DESCRIPTION OF THE DRAWINGS

Corresponding reference characters indicate corresponding parts throughout the several views. Elements in the drawings are not necessarily drawn to scale. The configurations shown in the drawings are merely examples, and should not be construed as limiting the scope of the invention in any manner.

DETAILED DESCRIPTION

A force and rotation sensing device can be suitable for measuring a force within a knee joint. A force sensor can measure a force exerted between opposing surfaces of a housing. A force display positioned on the housing can visually represent a value of the measured force, such as with a dual-sided light-emitting diode display that is visible from opposing sides of the housing. A first rotation sensor can measure a flexion/extension position of the housing. A flexion/extension display can visually represent a value of the measured flexion/extension position. In some examples, a zero button can set a reference orientation of the housing, so that the first rotation sensor can measure the flexion/extension position as a relative rotation with respect to the reference orientation. In some examples, circuitry can wirelessly transmit data corresponding to the value of the measured flexion/extension position, so that the value can be displayed on a device untethered to the housing.

Compared with visually estimating the angular position for the knee joint, the force and rotation sensing device improves the accuracy in determining the angular position. For example, for a surgical procedure that includes a step at which a surgeon is instructed to position a knee joint to a specified angle in extension, it is advantageous to use a device that can measure the actual knee joint angle and provide a numerical value to the surgeon, rather than relying on the surgeon's purely visual estimate of the knee joint angle. Such an improvement in accuracy can improve surgical results and repeatability.

Figure 1:
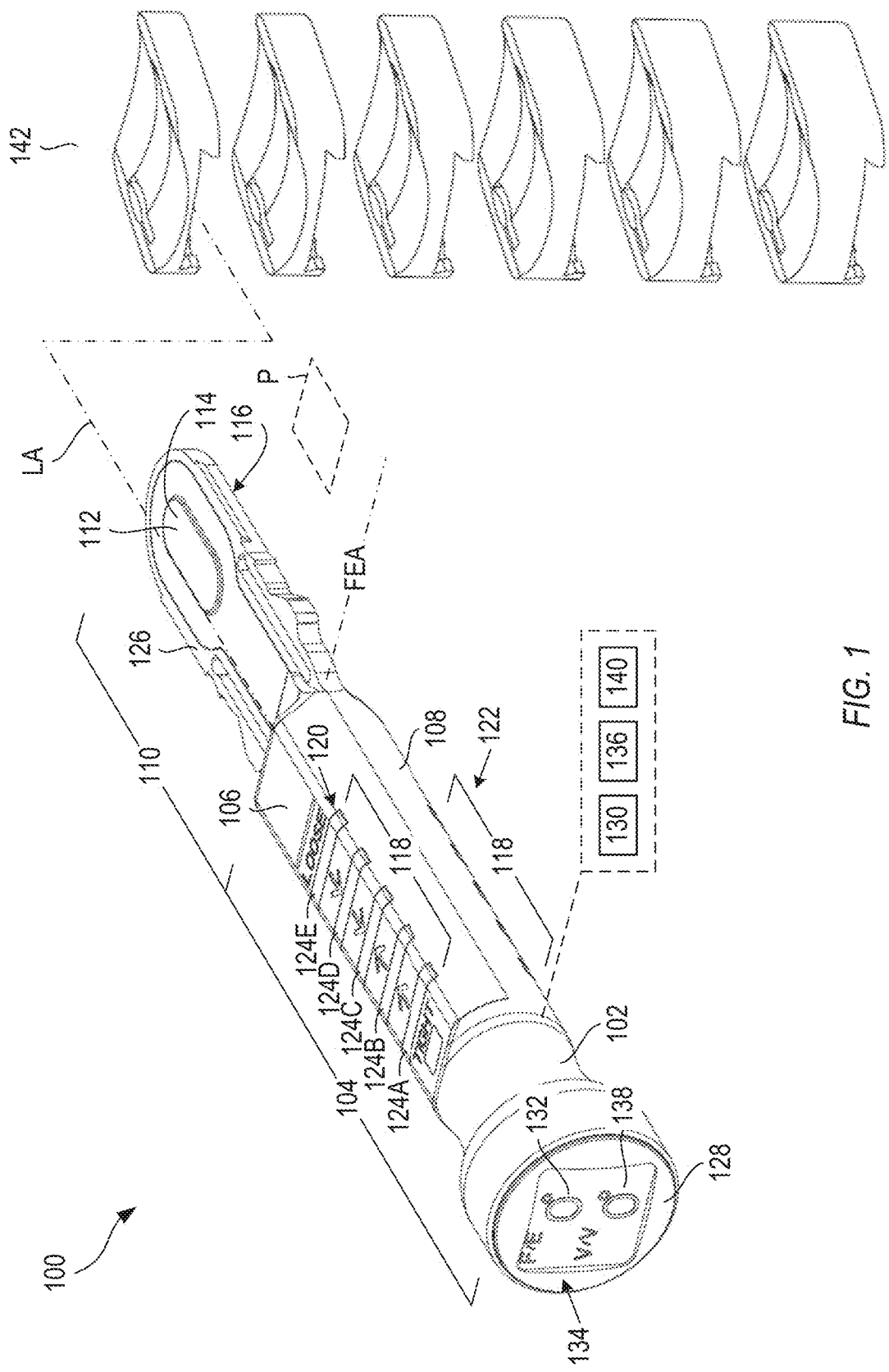
FIG. 1 shows a perspective view of a force and rotation sensing device, in accordance with some examples.

FIG. 1 shows a perspective view of a force and rotation sensing device 100, in accordance with some examples. The device 100 of FIG. 1 can be suitable for measuring a force within a knee joint. The configuration of FIG. 1 is but one example; other suitable configurations can also be used.

An elongate housing 102 can extend along a longitudinal axis (LA). A surgeon can grip and maneuver the housing 102 at a proximal portion 104 of the housing 102. In some examples, the proximal portion 104 of the housing 102 can include a generally cylindrical shape, with a flattened top portion 106 and a rounded bottom portion 108. In some examples, the flattened top portion 106 and the rounded bottom portion 108 can be separated by a proximal portion thickness. The surgeon can insert a distal portion 110 of the housing 102 into a knee joint during a procedure.

A force sensor 112 can measure a force exerted between opposing surfaces 114, 116 of the housing 102 at a distal portion 110 of the housing 102. In some examples, the opposing surfaces 114, 116 can be flat and parallel to each other. In some examples, the opposing surfaces 114, 116 can be parallel to the flattened top portion 106 of the proximal portion 104 of the housing 102. In some examples, the opposing surfaces 114, 116 can be separated by a distal portion thickness. In some examples, the distal portion thickness can be less than the proximal portion thickness. In some examples, the force sensor 112 can include a single element that measures the force. In other examples, the force sensor 112 can include multiple elements distributed across an area of the opposing surfaces 114, 116, which collectively measure the force when summed. In some examples, the force sensor 112 can be formed as one or more pressure sensors, which can measure a pressure exerted between the opposing surfaces 114, 116. The measured pressure can be integrated over an area of the opposing surfaces 114, 116 to yield a force value. For the purposes of this document, the term force sensor 112 can include one or more elements that measures force, and/or one or more elements that measures pressure.

A force display 118 can be positioned on the housing 102 and can visually represent a value of the measured force. In some examples, the force display 118 may not display the measured force directly, but instead can provide a visual indication of whether the measured force falls into one or more specified ranges or bins. In some examples, the bins can include five ranges, labeled for convenience as first, second, third, fourth, and fifth ranges. In some of these examples, the third range can represent a range of forces that can be deemed acceptable for a specified medical procedure. In some of these examples, the second range can represent a range of forces lower than the third range and directly adjacent to the third range. In some of these examples, the fourth range can represent a range of forces greater than the third range and directly adjacent to the fourth range. In some of these examples, the first range can extend from zero force (e.g., unbounded) to the lower edge of the second range. In some of these examples, the fifth range can extend from the upper edge of the fourth range and up (e.g., also unbounded). These are but examples of ranges or bins of specified force values; other suitable ranges can also be used.

In some examples, the force display 118 can include a dual-sided light-emitting diode (LED) display that is visible from opposing sides of the housing 102. In some examples, the opposing sides are a top 120 and a bottom 122 of the housing 102. For the five-bin example presented above, the force display 118 can include five LEDs 124A-E, arranged in a line along the housing 102. The first LED 124A, corresponding to the first bin, can be positioned at a proximal end of the line. The fifth LED 124E, corresponding to the fifth bin, can be positioned at a distal end of the line. The second, third, and fourth LEDs 124B-D can be positioned between the first and fifth LEDs 124A, 124E, sequentially along the line. In some examples, the LED display can include a specified color for each bin. For example, the third bin (corresponding to acceptable forces) can correspond to a green LED (e.g., if the measured force falls within the third range, the force display 118 lights up a green LED on the housing 102). The second and fourth bins (corresponding to nearly-acceptable forces) can correspond to orange or yellow LEDs. The first and fifth bins (corresponding to unacceptable forces) can correspond to red LEDs. During a surgical procedure, a surgeon can see the LED color from the surgeon's peripheral vision, so that the surgeon can sense the force value without having to devote significant attention to the force display 118. Using the color scheme described above, the surgeon can manipulate the knee joint to attempt to move the color from red, to orange or yellow, and ultimately to green. This color scheme is but one example; other suitable colors can also be used. In some examples, the LEDs can be positioned centrally in the housing 102, and can be seen from opposing sides of the housing 102. In other examples, the force display 118 includes two sets of LEDs, each visible from the top 120 and the bottom 122 of the housing 102.

A reference surface 126 can be positioned on the housing 102. In some examples, the reference surface 126 can be parallel to one or both of the opposing surfaces 114, 116. In some examples, the reference surface 126 can be formed as one of the opposing surfaces 114, 116. In some examples, the reference surface 126 can define a plane (P) that includes the longitudinal axis (LA). In some examples, the reference surface 126 can be parallel to the top 120 of the housing 102. The reference surface 126 can further define a flexion/extension axis (FEA) as being parallel to the plane (P) and perpendicular to the longitudinal axis (LA).

A calibration input 128 on the housing 102 can set a reference orientation of the housing 102. For example, during a surgical knee joint procedure, the surgeon can place the reference surface 126 of the housing 102 against a resected condyle in the knee joint, and use the calibration input 128 to set the reference orientation of the housing 102. The surgeon can then reposition the housing 102 as needed in the procedure. As the housing 102 is repositioned, the display on the housing 102 (or on a device external to the housing 102) can provide angular measurements of the housing's orientation, with respect to the reference orientation. In some examples, the calibration input 128 can be positioned on a proximal end of the housing 102, although other suitable locations on the housing 102 can also be used. In some examples, the calibration input 128 can be a zero button, so that when a surgeon depresses the zero button, the housing 102 can set the reference orientation of the housing 102, and angular motion of the housing 102 can be measured relative to the reference orientation.

A first rotation sensor 130 can measure a flexion/extension position of the housing 102. The flexion/extension position can be a relative rotational position about the flexion/extension axis (FEA) with respect to the reference orientation. The first rotation sensor 130 can include at least one of an accelerometer or a gyroscope.

A flexion/extension display 132 can visually represent a value of the measured flexion/extension position. In some examples, the flexion/extension display 132 can be positioned on a proximal end 134 of the housing 102, opposite the distal portion 110. In some examples, the flexion/extension display 132 can display a numeric representation of the measured flexion/extension position in degrees. In some examples, in which the calibration input 128 is a zero button positioned on the proximal end 134 of the housing 102, the flexion/extension display 132 can be positioned on the zero button.

In some examples, such as those shown in FIGS. 3-8 and discussed below, the flexion/extension angle can have a value of zero at the orientation at which the zero button is pushed, and can increase in value as a knee joint is positioned into extension. For these examples, a surgeon can position the knee joint until the flexion/extension display 132 shows a specified value, such as 110 degrees. Alternatively, there may be instances when the surgeon prefers to position the knee joint to achieve a value of zero on the flexion/extension display 132. For these cases, the flexion/extension angle can have a specified value, such as 110 degrees, at the orientation at which the zero button is pushed, and can decrease in value to zero as the knee joint is positioned into extension. In some examples, the device can store multiple angular configurations, and can be switched among the stored configurations. Other suitable angular configurations can also be used.

A second rotation sensor 136 can measure a varus/valgus position of the housing 102. The varus/valgus position can be a relative rotational position about the longitudinal axis (LA) with respect to the reference orientation. The second rotation sensor 136 can include at least one of an accelerometer or a gyroscope.

A varus/valgus display 138 can visually represent a value of the measured varus/valgus position. In some examples, the vanes/valgus display 138 can be positioned on the proximal end 134 of the housing 102. In some examples, the varus/valgus display 138 can be positioned adjacent to the flexion/extension display 132. In some examples, the varus/valgus display 138 can be positioned on the proximal end 134 of the housing 102. In some examples, the varus/valgus display 138 can display a numeric representation of the measured varus/valgus position in degrees.

Circuitry 140 can wirelessly transmit data corresponding to the value of the measured flexion/extension position and the value of the measured vanes/valgus position. In some examples, the values can be displayed on a device wirelessly connected to the circuitry 140 in the housing 102, either directly or through a network. For example, the circuitry 140 can connect wirelessly or through a wired connection to a computer (directly or through a network), and the computer can display one or both of the measured values on a monitor.

For some surgical procedures, a surgeon can use the device 100 to determine a thickness of an implantable element, such as an implantable femoral component. These procedures can additionally use a plurality of shims 142 of different thicknesses. Each shim 142 can be removably attachable to the distal portion 110 of the housing 102 over one of the opposing surfaces 114, 116, so that the force sensor 112 measures a force exerted between the shim 142 and the other of the opposing surfaces 114, 116. During such a procedure, the surgeon can attach a shim 142 of a particular thickness, insert the device 100 and shim 142 into the knee joint, position the knee joint at one or more specified positions between full flexion and full extension, and read a measured force from the force display 118 at the one or more specified positions. If the measured force is too large at the one or more specified positions, the surgeon can repeat the measurement with a thinner shim 142. Likewise, if the measured force is too small at the one or more specified positions, the surgeon can repeat the measurement with a thicker shim 142. Once the measured force is in the acceptable range at the one or more specified positions, the shim thickness that produced the acceptable results can determine a suitable size of an implant for the knee joint. In some examples, such as for an implantable femoral component that has a convex outer surface, each shim 142 may have a corresponding concave surface positioned to contact the convex outer surface of the implantable femoral component. In some examples, the concave curvature may be along only one dimension, so that a cross-section of the shim 142 may be the same for various locations on the shim 142 along the longitudinal axis of the housing 102. In some examples, the shims 142 can snap onto and off the distal portion 110 of the housing 102, over one of the opposing surfaces 114, 116.

Figure 2:
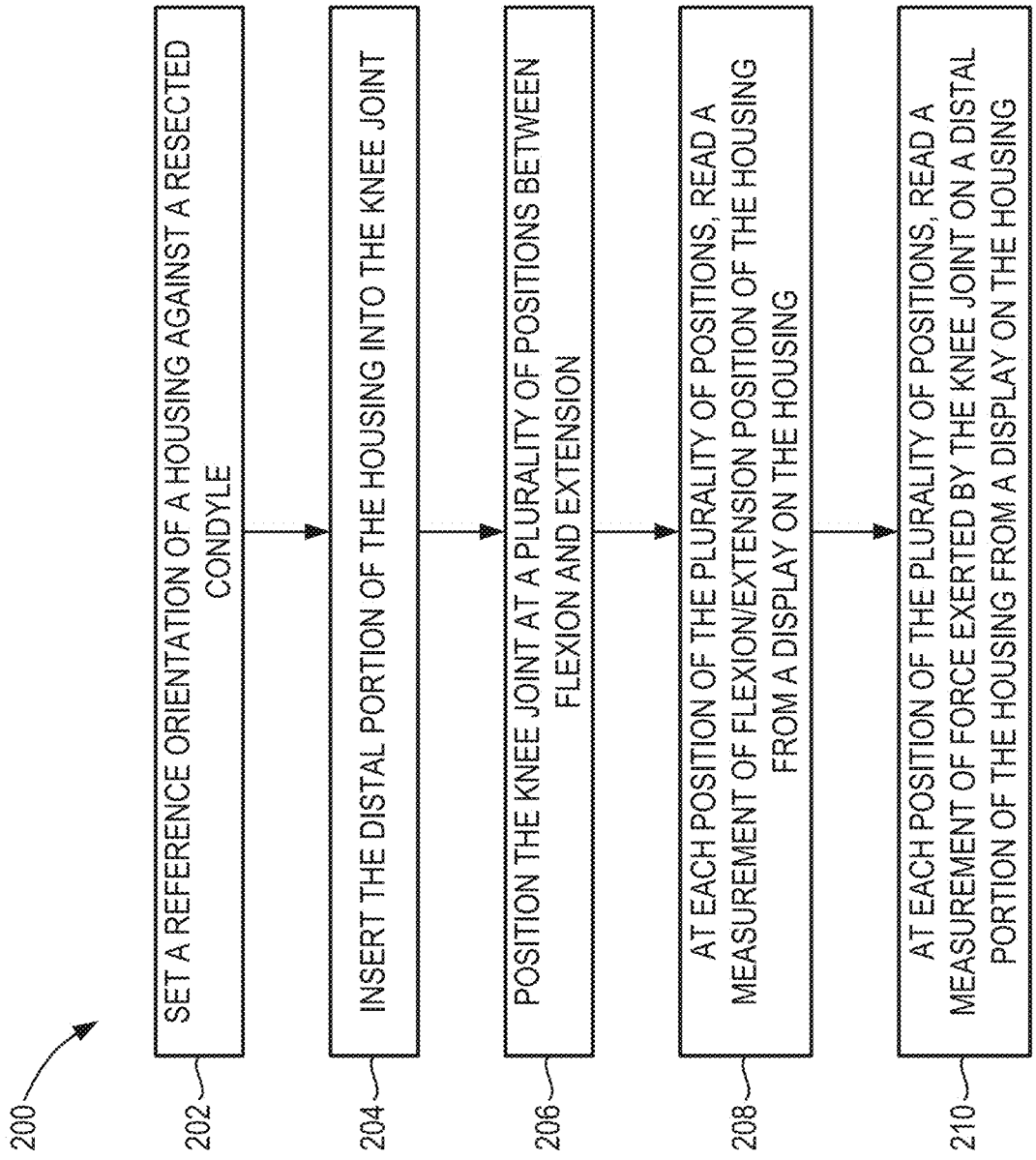
FIG. 2 shows a flowchart of a method for measuring force within a knee joint, in accordance with some examples.

FIG. 2 shows a flowchart of a method 200 for measuring force within a knee joint, in accordance with some examples. A surgeon can use the method to determine a suitable size of an implantable element in a knee joint, such as an implantable femoral component. The method 200 of FIG. 2 is but one method for measuring force within a knee joint. Other suitable methods can also be used.

Figure 3:
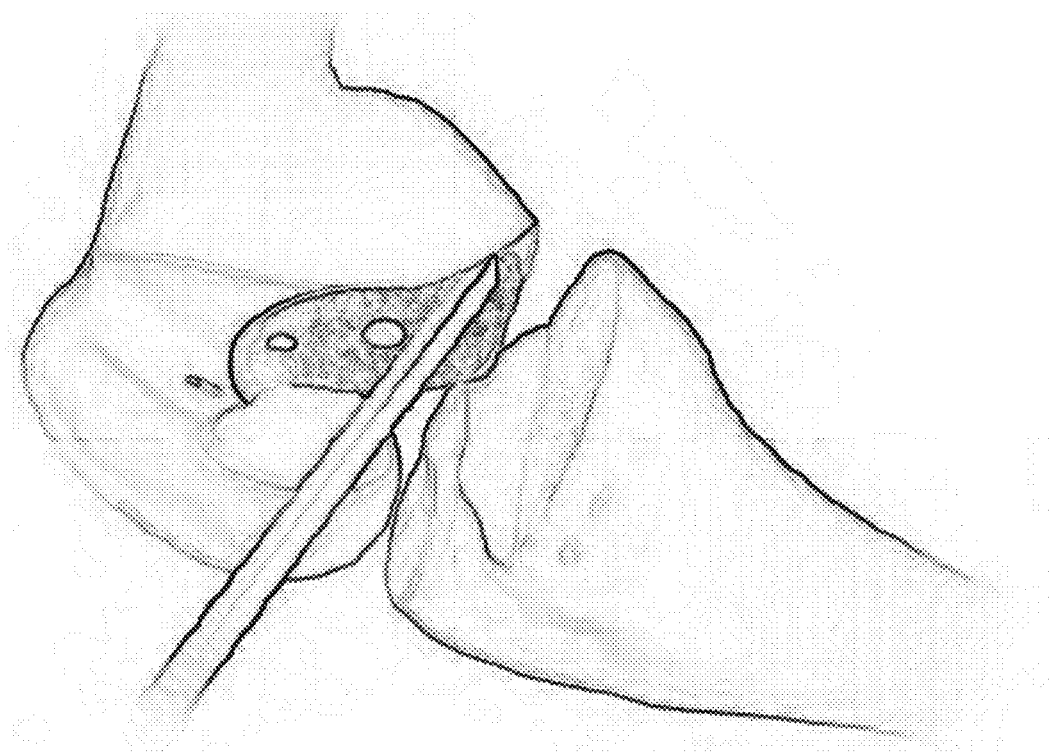
FIG. 3 shows an example of a knee joint after resections and milling have been performed, prior to executing the method of FIG. 2.

Prior to executing the method 200, a surgeon can complete a tibial resection, a posterior femoral resection, and O spigot milling. FIG. 3 shows an example of a knee joint after these resections and milling have been performed, prior to executing the method 200.

Figure 4:
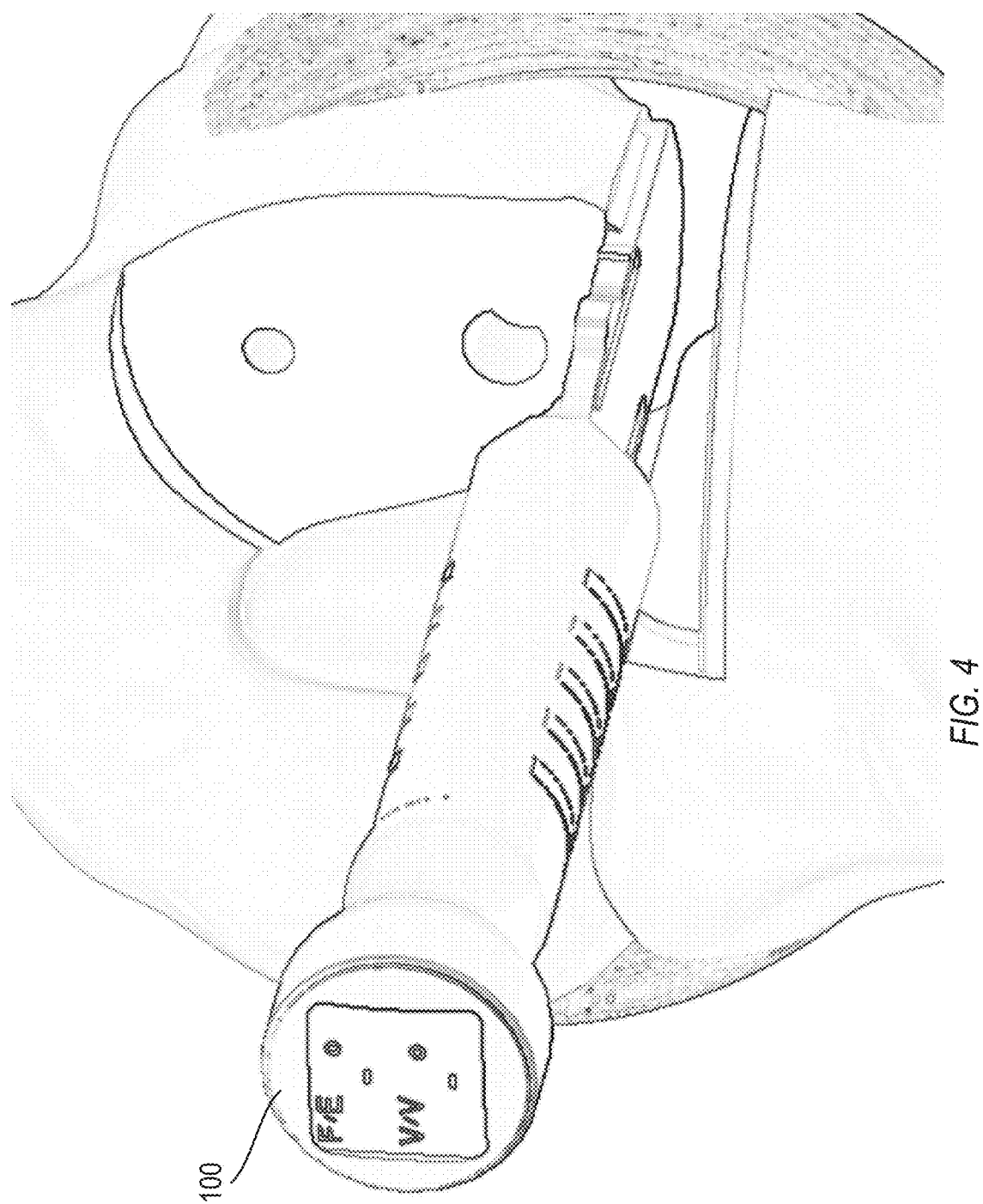
FIG. 4 shows an example of a housing having its reference surface positioned in contact with the resected condyle, during execution of the method of FIG. 2.
Figure 5:
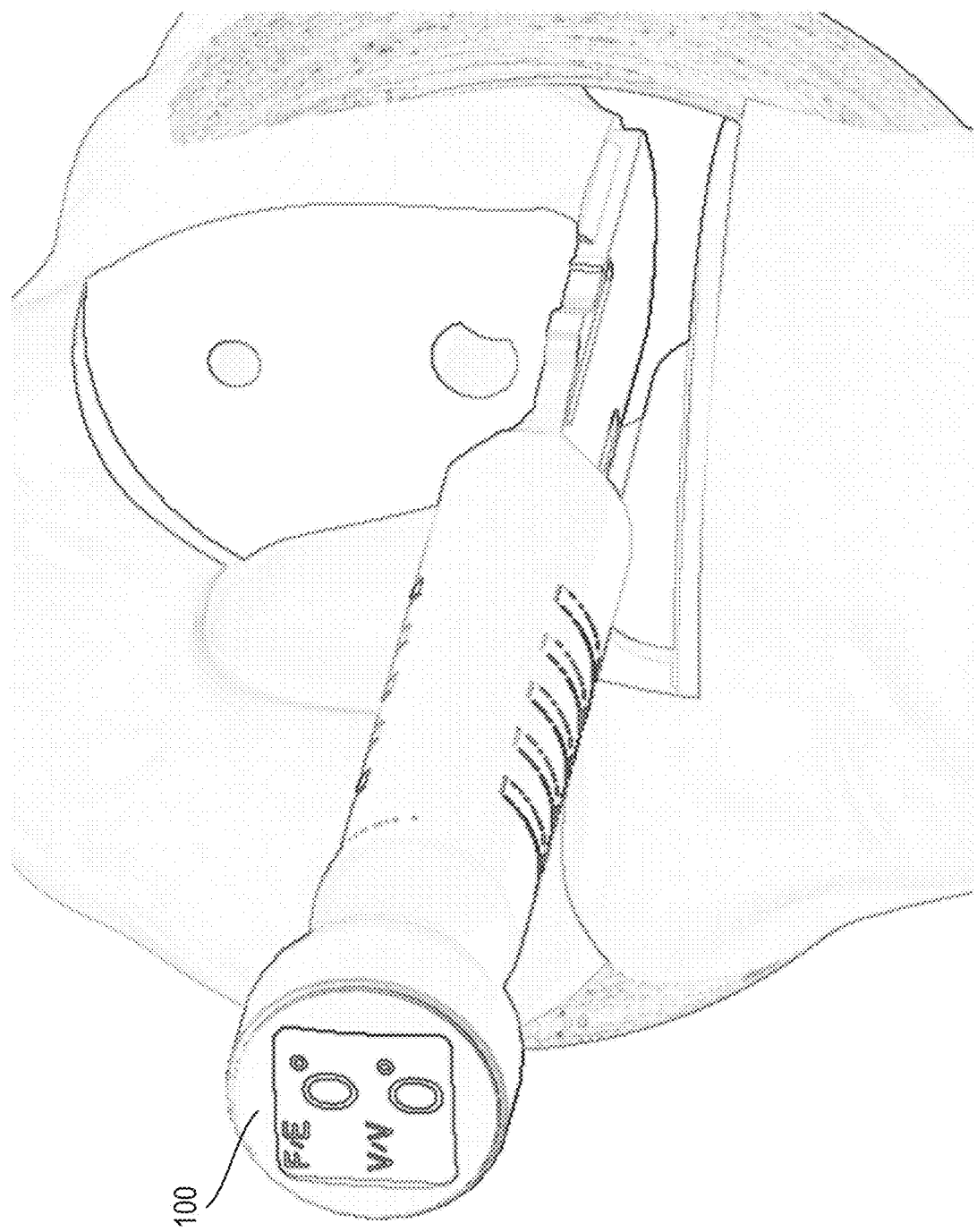
FIG. 5 shows an example of a housing after setting the reference orientation of the housing, during execution of the method of FIG. 2.

At operation 202, the surgeon can set a reference orientation of a housing against a resected condyle in a knee joint. FIG. 4 shows an example of a housing having its reference surface positioned in contact with the resected condyle. In FIG. 5, the flexion/extension display (labeled "F/E") and varus/valgus display (labeled "V/V") do not yet show angular values. The surgeon then can depress the zero button on the housing to set the reference orientation of the housing, so that angular motion of the housing can be measured relative to the reference orientation. In FIG. 5, the zero button has been depressed, and the flexion/extension display and the varus/valgus display show angular values of zero.

After setting the reference orientation of the housing, the surgeon can attach a provisional femoral component to the resected femur. The provisional femoral component can have a convex curved surface facing the tibia. The surgeon can attach a shim of a particular thickness to the distal portion of the housing.

Figure 6:
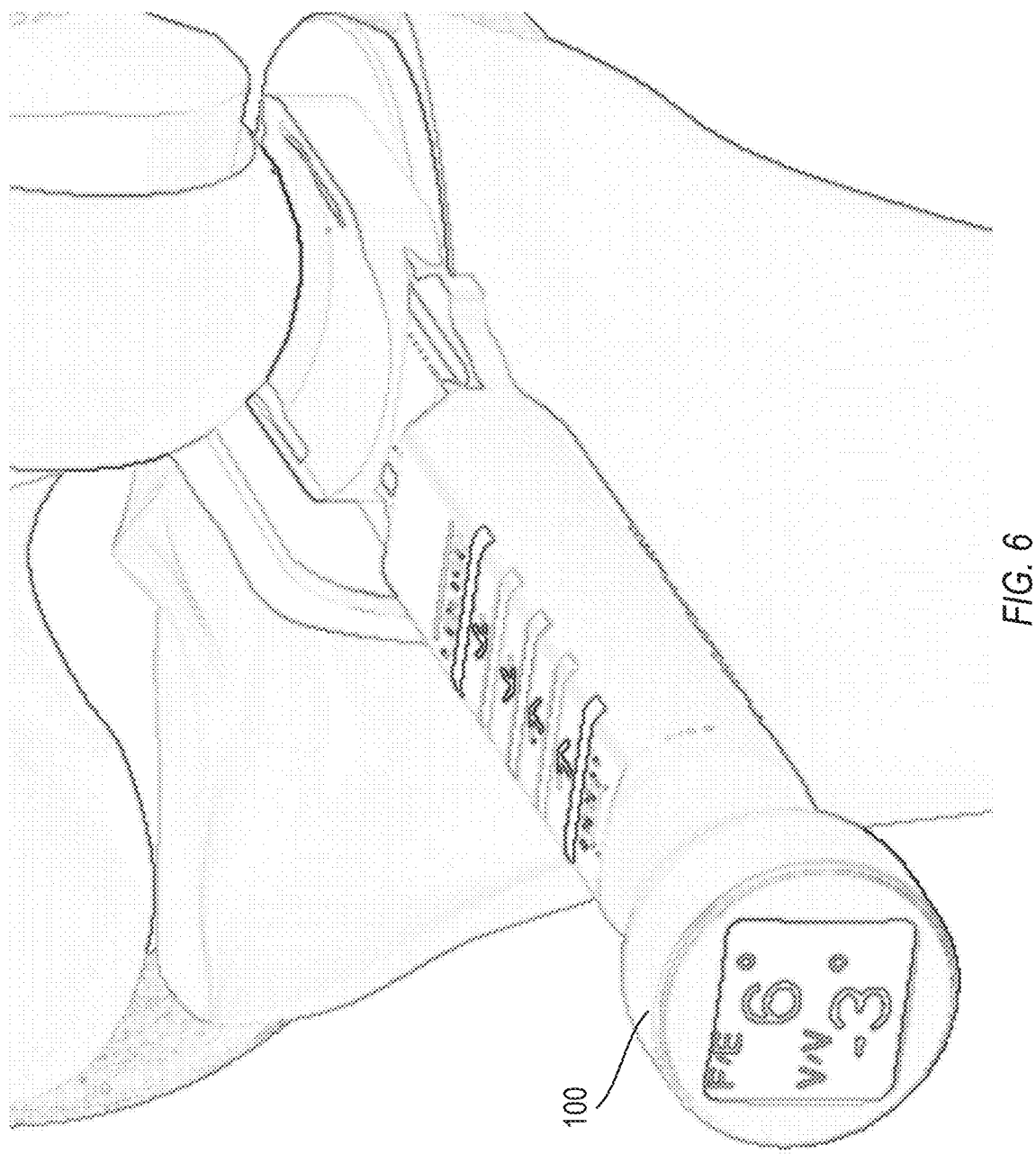
FIG. 6 shows an example of the housing and shim inserted into the knee joint, during execution of the method of FIG. 2.

At operation 204, the surgeon can insert the distal portion of the housing into the knee joint, the distal portion of the housing including a force sensor. The surgeon can position the housing and shim in the joint space until the housing and shim are seated. FIG. 6 shows an example of the housing and shim inserted into the knee joint. In the example of FIG. 6, the flexion/extension display shows an angular value of positive six degrees, and the varus/valgus display shows an angular value of negative three degrees.

At operation 206, the surgeon can position the knee joint at a plurality of positions between flexion and extension, inclusive.

At operation 208, the surgeon can, at each position of the plurality of positions, read a measurement of flexion/extension position of the housing from a display on the housing.

At operation 210, the surgeon can, at each position of the plurality of positions, read a measurement of force exerted by the knee joint on a distal portion of the housing from a display on the housing.

Figure 7:
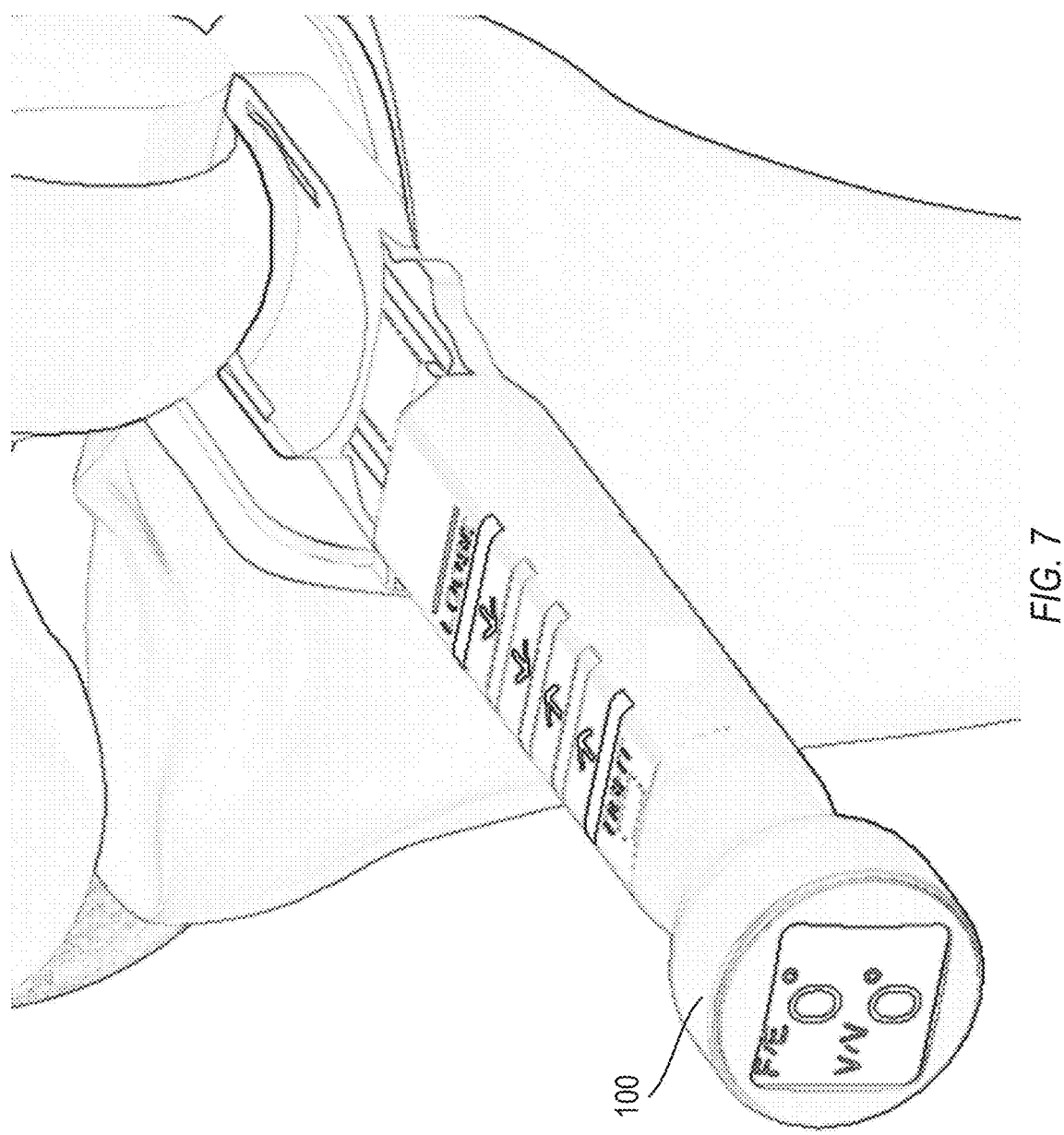
FIG. 7 shows an example of the housing and shim inserted into the knee joint, with the knee joint in flexion.

In the example of FIG. 7, the surgeon has positioned the knee joint in flexion, so that the flexion/extension display reads zero degrees. In this example, the varus/valgus display also reads zero degrees; in some examples, the surgeon may monitor the varus/valgus angle, but not position the knee joint to actively set the varus/valgus angle to zero.

Figure 8:
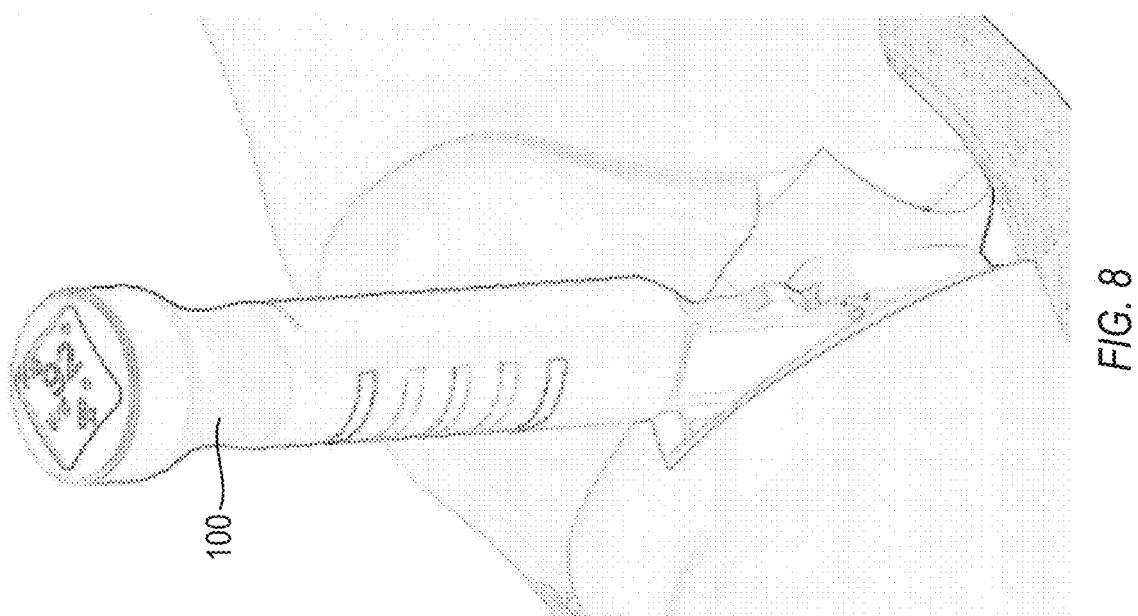
FIG. 8 shows an example of the housing and shim inserted into the knee joint, with the knee joint in extension.

In the example of FIG. 8, the surgeon has positioned the knee joint in extension, so that the flexion/extension display reads positive ninety-two degrees. In this example, the vanes/valgus display reads positive four degrees.

To further illustrate the device and related method disclosed herein, a non-limiting list of examples is provided below. Each of the following non-limiting examples can stand on its own, or can be combined in any permutation or combination with any one or more of the other examples.

In Example 1, a force and rotation sensing device can include: an elongate housing extending along a longitudinal axis; a force sensor configured to measure a force exerted between opposing surfaces of the housing at a distal portion of the housing; a force display positioned on the housing and configured to visually represent a value of the measured force; a reference surface positioned on the housing, the reference surface defining a plane that includes the longitudinal axis, the reference surface further defining a flexion/extension axis as being parallel to the plane and perpendicular to the longitudinal axis; a first rotation sensor configured to measure a flexion/extension position of the housing, the flexion/extension position being a rotational position about the flexion/extension axis; and a flexion/extension display positioned on the housing and configured to visually represent a value of the measured flexion/extension position.

In Example 2, the force and rotation sensing device of Example 1 can optionally further include a calibration input on the housing, the calibration input configured to set a reference orientation of the housing, the first rotation sensor further configured to measure the flexion/extension position as a relative rotation with respect to the reference orientation.

In Example 3, the force and rotation sensing device of any one of Examples 1-2 can optionally be configured such that the flexion/extension display is positioned on a proximal end of the housing, opposite the distal portion.

In Example 4, the force and rotation sensing device of any one of Examples 1-3 can optionally be configured such that the calibration input is a zero button positioned on the proximal end of the housing; and the flexion/extension display is positioned on the zero button.

In Example 5, the force and rotation sensing device of any one of Examples 1-4 can optionally be configured such that the flexion/extension display is configured to display a numeric representation of the measured flexion/extension position in degrees.

In Example 6, the force and rotation sensing device of any one of Examples 1-5 can optionally further include circuitry configured to wirelessly transmit data corresponding to the value of the measured flexion/extension position.

In Example 7, the force and rotation sensing device of any one of Examples 1-6 can optionally be configured such that the force display includes a dual-sided light-emitting diode display that is visible from opposing sides of the housing.

In Example 8, the force and rotation sensing device of any one of Examples 1-7 can optionally be configured such that the opposing surfaces are parallel to each other and to the reference surface.

In Example 9, the force and rotation sensing device of any one of Examples 1-8 can optionally be configured such that the reference surface is formed as one of the opposing surfaces.

In Example 10, the force and rotation sensing device of any one of Examples 1-9 can optionally further include a plurality of shims of different thicknesses, each shim being removably attachable to the distal portion of the housing over one of the opposing surfaces, so that the force sensor measures a force exerted between the shim and the other of the opposing surfaces.

In Example 11, the force and rotation sensing device of any one of Examples 1-10 can optionally be configured such that the first rotation sensor includes at least one of an accelerometer or a gyroscope.

In Example 12, the force and rotation sensing device of any one of Examples 1-11 can optionally further include a second rotation sensor configured to measure a varus/valgus position of the housing, the varus/valgus position being a rotational position about the longitudinal axis.

In Example 13, the force and rotation sensing device of any one of Examples 1-12 can optionally further include a calibration input on the housing, the calibration input configured to set a reference orientation of the housing, the first rotation sensor further configured to measure the flexion/extension position as a relative rotation with respect to the reference orientation, the second rotation sensor further configured to measure the varus/valgus position as a relative rotation with respect to the reference orientation.

In Example 14, the force and rotation sensing device of any one of Examples 1-13 can optionally further include a varus/valgus display configured to visually represent a value of the measured varus/valgus position.

In Example 15, the force and rotation sensing device of any one of Examples 1-14 can optionally be configured such that the varus/valgus display is configured to display a numeric representation of the measured varus/valgus position in degrees.

In Example 16, the force and rotation sensing device of any one of Examples 1-15 can optionally be configured such that the flexion/extension display and the varus/valgus display are positioned on a proximal end of the housing, opposite the distal portion.

In Example 17, the force and rotation sensing device of any one of Examples 1-16 can optionally further include circuitry configured to wirelessly transmit data corresponding to the value of the measured flexion/extension position and the value of the measured varus/valgus position.

In Example 18, a method for measuring force within a knee joint can include: setting a reference orientation of a housing against a resected condyle in a knee joint; inserting a distal portion of the housing into the knee joint, the distal portion of the housing including a force sensor; positioning the knee joint at a plurality of positions between flexion and extension, inclusive; at each position of the plurality of positions, reading a measurement of flexion/extension position of the housing from a display on the housing; and at each position of the plurality of positions, reading a measurement of force exerted by the knee joint on a distal portion of the housing from a display on the housing.

In Example 19, a force and rotation sensing device can include: an elongate housing extending along a longitudinal axis; a force sensor configured to measure a force exerted between opposing surfaces of the housing at a distal portion of the housing; a force display positioned on the housing and configured to visually represent a value of the measured force, the force display including a dual-sided light-emitting diode display that is visible from opposing sides of the housing; a reference surface positioned on the housing and formed as one of the opposing surfaces, the reference surface defining a plane that includes the longitudinal axis, the reference surface further defining a flexion/extension axis as being parallel to the plane and perpendicular to the longitudinal axis; a zero button on the housing, the zero button configured to set a reference orientation of the housing; a first rotation sensor configured to measure a flexion/extension position of the housing, the flexion/extension position being a relative rotational position about the flexion/extension axis with respect to the reference orientation, the first rotation sensor including at least one of an accelerometer or a gyroscope; a flexion/extension display positioned on a proximal end of the housing, opposite the distal portion, the flexion/extension display configured to visually represent a value of the measured flexion/extension position; a second rotation sensor configured to measure a varus/valgus position of the housing, the varus/valgus position being a relative rotational position about the longitudinal axis with respect to the reference orientation, the second rotation sensor including at least one of an accelerometer or a gyroscope; a varus/valgus display positioned on the proximal end of the housing, the varus/valgus display configured to visually represent a value of the measured varus/valgus position; and circuitry configured to wirelessly transmit data corresponding to the value of the measured flexion/extension position and the value of the measured varus/valgus position.

In Example 20, the force and rotation sensing device of Example 19 can optionally further include a plurality of shims of different thicknesses, each shim being removably attachable to the distal portion of the housing over one of the opposing surfaces, so that the force sensor measures a force exerted between the shim and the other of the opposing surfaces.

While this invention has been described as having example designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A force and rotation sensing device, comprising:
   an elongate housing extending along a longitudinal axis;
   a force sensor configured to measure a force exerted between opposing surfaces of the housing at a distal portion of the housing;
   a force display positioned on the housing and configured to visually represent a value of the measured force;
   a reference surface positioned on the housing, the reference surface defining a plane that includes the longitudinal axis, the reference surface further defining a flexion/extension axis as being parallel to the plane and perpendicular to the longitudinal axis;
   a first rotation sensor configured to measure a flexion/extension position of the housing, the flexion/extension position being a rotational position about the flexion/extension axis;
   a flexion/extension display positioned on the housing and configured to visually represent a value of the measured flexion/extension position; and
   a zero button located on a proximal end of the housing opposite the distal portion, the zero button configured to set a reference orientation of the housing, the first rotation sensor further configured to measure the flexion/extension position as a relative rotation with respect to the reference orientation.

2. The force and rotation sensing device of claim 1, wherein the flexion/extension display is positioned on the proximal end of the housing.

3. The force and rotation sensing device of claim 2, wherein the flexion/extension display is positioned on the zero button.

4. The force and rotation sensing device of claim 1, wherein the flexion/extension display is configured to visually represent the measured flexion/extension position in degrees.

5. The force and rotation sensing device of claim 1, further comprising circuitry configured to wirelessly transmit data corresponding to the value of the measured flexion/extension position.

6. The force and rotation sensing device of claim 1, wherein the force display includes a dual-sided light-emitting diode display that is visible from opposing sides of the housing.

7. The force and rotation sensing device of claim 1, wherein the opposing surfaces are parallel to each other and to the reference surface.

8. The force and rotation sensing device of claim 1, wherein the reference surface is formed as one of the opposing surfaces.

9. The force and rotation sensing device of claim 1, further comprising a plurality of shims of different thicknesses, each shim being removably attachable to the distal portion of the housing over one of the opposing surfaces, so that the force sensor measures a force exerted between the shim and the other of the opposing surfaces.

10. The force and rotation sensing device of claim 1, wherein the first rotation sensor includes at least one of an accelerometer or a gyroscope.

11. A force and rotation sensing device, comprising:
    an elongate housing extending along a longitudinal axis;
    a force sensor configured to measure a force exerted between opposing surfaces of the housing at a distal portion of the housing;
    a force display positioned on the housing and configured to visually represent a value of the measured force;
    a reference surface positioned on the housing, the reference surface defining a plane that includes the longitudinal axis, the reference surface further defining a flexion/extension axis as being parallel to the plane and perpendicular to the longitudinal axis;
    a first rotation sensor configured to measure a flexion/extension position of the housing, the flexion/extension position being a rotational position about the flexion/extension axis;
    a flexion/extension display positioned on the housing and configured to visually represent a value of the measured flexion/extension position; and a second rotation sensor configured to measure a varus/valgus position of the housing, the varus/valgus position being a rotational position about the longitudinal axis.

12. The force and rotation sensing device of claim 11, further comprising a calibration input on the housing, the calibration input configured to set a reference orientation of the housing, the first rotation sensor further configured to measure the flexion/extension position as a relative rotation with respect to the reference orientation, the second rotation sensor further configured to measure the varus/valgus position as a relative rotation with respect to the reference orientation.

13. The force and rotation sensing device of claim 12, further comprising a varus/valgus display configured to visually represent a value of the measured varus/valgus position.

14. The force and rotation sensing device of claim 13, wherein the varus/valgus display is configured to display a numeric representation of the measured varus/valgus position in degrees.

15. The force and rotation sensing device of claim 13, wherein the flexion/extension display and the varus/valgus display are positioned on a proximal end of the housing, opposite the distal portion.

16. The force and rotation sensing device of claim 11, further comprising circuitry configured to wirelessly transmit data corresponding to the value of the measured flexion/extension position and the value of the measured varus/valgus position.

17. A method for measuring force within a knee joint, the method comprising:
  setting a reference orientation of a housing against a resected condyle in a knee joint by depressing a zero button located on a proximal end of the housing;
  inserting a distal portion of the housing into the knee joint, the distal portion of the housing being opposite the proximal end and including a force sensor;
  positioning the knee joint at a plurality of positions between flexion and extension, inclusive;
  at each position of the plurality of positions, reading a measurement of flexion/extension position of the housing from a display on the housing, the display configured to display one or more numerals that represent the measured flexion/extension position; and
  at each position of the plurality of positions, reading a measurement of force exerted by the knee joint on a distal portion of the housing from a display on the housing.

18. A force and rotation sensing device, comprising:
  an elongate housing extending along a longitudinal axis;
  a force sensor configured to measure a force exerted between opposing surfaces of the housing at a distal portion of the housing;
  a force display positioned on the housing and configured to visually represent a value of the measured force, the force display including a dual-sided light-emitting diode display that is visible from opposing sides of the housing;
  a reference surface positioned on the housing and formed as one of the opposing surfaces, the reference surface defining a plane that includes the longitudinal axis, the reference surface further defining a flexion/extension axis as being parallel to the plane and perpendicular to the longitudinal axis;
  a zero button on the housing, the zero button configured to set a reference orientation of the housing;
  a first rotation sensor configured to measure a flexion/extension position of the housing, the flexion/extension position being a relative rotational position about the flexion/extension axis with respect to the reference orientation, the first rotation sensor including at least one of an accelerometer or a gyroscope;
  a flexion/extension display positioned on a proximal end of the housing, opposite the distal portion, the flexion/extension display configured to visually represent a value of the measured flexion/extension position;
  a second rotation sensor configured to measure a varus/valgus position of the housing, the varus/valgus position being a relative rotational position about the longitudinal axis with respect to the reference orientation, the second rotation sensor including at least one of an accelerometer or a gyroscope;
  a varus/valgus display positioned on the proximal end of the housing, the varus/valgus display configured to visually represent a value of the measured varus/valgus position; and
  circuitry configured to wirelessly transmit data corresponding to the value of the measured flexion/extension position and the value of the measured varus/valgus position.

19. The force and rotation sensing device of claim 18, further comprising a plurality of shims of different thicknesses, each shim being removably attachable to the distal portion of the housing over one of the opposing surfaces, so that the force sensor measures a force exerted between the shim and the other of the opposing surfaces.

* * * * *